United States Patent [19]

Lewis et al.

[11] Patent Number: 4,761,278

[45] Date of Patent: Aug. 2, 1988

[54] LADIES AFTERSHAVE PREPARATION AND METHOD FOR ITS MANUFACTURE

[76] Inventors: Jean Lewis, P.O. Box 34, Patagonia, Ariz. 85624; Michael De Chicio, P.O. Box 585, Sonoita, Ariz. 85637; Deborah Marshall, 750-B Falcon St., Austin, Tex. 78719

[21] Appl. No.: 25,819

[22] Filed: Mar. 13, 1987

[51] Int. Cl.$^4$ .................. A61K 7/15; A61K 31/14
[52] U.S. Cl. .................................................. 424/73
[58] Field of Search ................ 424/73, DIG. 13, 20

[56] References Cited

U.S. PATENT DOCUMENTS

| | | | |
|---|---|---|---|
| 2,987,446 | 6/1961 | Riethmueller | 424/73 |
| 4,234,450 | 11/1980 | Hirayama et al. | 424/73 X |
| 4,478,853 | 10/1984 | Chaussee | 424/73 X |
| 4,585,650 | 4/1986 | Newberry et al. | 424/73 |

*Primary Examiner*—Nancy A. B. Swisher
*Attorney, Agent, or Firm*—Richard C. Litman

[57] ABSTRACT

An improved ladies after shave preparation and its method for its manufacture consisting essentially of an astringent such as alcohol and propylene glycol in an amount of alcohol within the range of from about 52% to about 58% and in an amount of propylene glycol within the range of from about 7% to about 13%, by weight, a skin soothing and healing compound such as aloe vera in an amount within the range of from about 3% to about 5% by weight, a citric acid in an amount within the range of from about 0.8% to about 1.2% by weight, water in an amount within the range of from about 27% to about 33% by weight, sodium benzoate in an amount within a range of about 0.1% by weight, and a fragrance in an amount within a range of about 0.1% by weight.

2 Claims, No Drawings

LADIES AFTERSHAVE PREPARATION AND METHOD FOR ITS MANUFACTURE

BACKGROUND OF THE INVENTION

1. Field Of The Invention

The invention relates to an improved ladies aftershave preparation and method for its manufacture, and more particularly the invention is directed to a preparation for women who may shave tender skin areas as underarms and their legs, such areas that are not sufficiently toughened by normal exposure to the elements or the daily shaving of one's face as experienced with men. The product or preparation is seen to basically include an amount of aloe vera, a well known skin product having some well known soothing and healing properties.

The invention relates further to an improved ladies aftershave preparation and the method for its manufacture consisting essentially of an astringent such as alcohol and propylene gylcol in which an amount of alcohol is within the range of from about 52% to about 58% and in which an amount of propylene glycol is within the range of from about 7% to about 13%, by weight, a skin soothing and healing compound such as aloe vera in an amount within the range of from about 3% to about 5% by weight, a citric acid in an amount within the range of from about 0.8% to about 1.2% by weight, water in an amount within the range of from about 27% to about 33% by weight, sodium benzoate in an amount within a range of about 0.1% by weight, and a fragrance in an amount within a range of about 0.1% by weight, thereof as more particularly described herein.

2. Description Of The Prior Art

Various prior art after shave preparations and the method for its manufacture, and the like, as well as apparatus and method of their construction in general, are found to be known and exemplary of the U.S. prior art are the following:

U.S. Pat. No. 3,708,435: J. H. Starkman
U.S. Pat. No. 4,264,592: K. Xhajanka
U.S. Pat. No. 4,279,891: H. H Henkel et al
U.S. Pat. No. 4,318,900: D. G. Roswell et al
U.S. Pat. No. 4,369,180: D. M. Mihalovits
U.S. Pat. No. 4,482,537: E. El-Memshawy et al
U.S. Pat. No. 4,505,902: M. A. Millard Chemical Formulary, Vol. 25, pages 156, 158, 186, 187 and 190; and Vol. 26, pages 121, 122, 127 and 141.

Mihalovits discloses a cosmetic facial preparation containing aloe vera which is a main ingredient; the preparation cleanses and softens the skin and improves the texture, and it contains aloe vera, cornstarch or cosmetic clay, albumin allantoin and vitamins.

Mollard discloses a skin treatment preparation that provides moisture in the promotion of healing and produces a pleasing cosmetic effect. It comprises a small amount of aloe vera juice, mineral oil, apricot kernal oil, some preservatives and other ingredients.

Starkman discloses a method of cleaning human skin in which the preparation comprises a small amount of aloe vera juice, mineral oil, apricot kernal oil, some preservatives and other ingredients.

Starkman discloses a method of cleaning human skin in which the preparation comprises four major ingredients of an aftershave lotion, namely, water, alcohol, propylene glycol and a fragrance agent.

These patents or known prior uses teach and disclose various types of cosmetic preparations of sorts and of various manufactures and the like as well as methods of their manufacture, but none of them whether taken singly or in combination disclose the specific details of the combination of the invention in such a way as to bear upon the claims of the present invention.

SUMMARY OF THE INVENTION

An object, advantage and feature of the invention is to provide a novel and improved ladies aftershave preparation and the method for its manufacture consisting essentially of alcohol in an amount within the range of from about 52% to about 58% by weight, propylene glycol within the range of from about 7% to about 13% by weight, a skin soothing and healing compound such as aloe vera in an amount within the range of from about 3% to about 5% by weight, a citric acid in an amount within the range of from about 0.8% to about 1.2% by weight, water in an amount within the range of from about 27% to about 33% by weight, and a fragrance in an amount within a range of about 0.1% by weight.

A further object of the invention is wherein the alcohol is in an amount of about 55% by weight, the propylene glycol is in an amount of about 10% by weight, the aloe vera is in an amount of about 4% by weight, the citric acid is in an amount of less than 1.0% by weight, the water is in an amount of 30% by weight, the sodium benzoate is in an amount of 0.1% by weight and the fragrance is in an amount of 0.1% by weight.

Another object of the invention is directed further to a product that performs as a ladies aftershave lotion that provides immediate cooling and soothing, evaporates quickly, smells pleasant, makes the skin feel and look smooth and soft, and has no adverse reaction with skin or clothes of the user, and is such a pleasant change from shaving without using anything afterwards that the user would not think of going back to not using the product.

These together with other objects and advantages which will become subsequently apparent reside in the details of the process and operation thereof as more fully hereinafter is described and claimed, reference being had to the accompanying description.

DESCRIPTION OF A PREFERRED EMBODIMENT OF THE INVENTION

Referring now to the specific details of the invention there is an improved ladies aftershave preparation and its method for its manufacture comprising essentially of an astringent such as alcohol and propylene glycol in an amount of alcohol within the range of from about 52% to about 58% and in an amount of propylene glycol within the range of from about 7% to about 13%, by weight, a skin soothing and healing compound such as aloe vera in an amount within the range of from about 3% to about 5% by weight, a citric acid in an amount within the range of from about 0.8% to about 1.2% by weight, water in an amount within the range of from about 27% to about 33% by weight, sodium benzoate in an amount within a range of about 0.1% by weight, and a fragrance in an amount within a range of about 0.1% by weight.

The steps of making the composition are (1) add citric acid and sodium benzoate to aloe vera as sequestering agents, (2) add aloe vera solution to water, then (3) mix the remaining ingredients with the watered down aloe vera in the desired combination, being sure to add fragrance after adding alcohol to prevent the fragrance from suspension if using a pure oil of essence. It is found that to add alcohol or propylene glycol at step (2) would cause mixing problems making the aloe vera suspend, even after adding water at a later point in time.

Another example of the product or preparation the alcohol (SDA40) is in an amount of about 55% by weight, the propylene glycol is in an amount of about 10% by weight, the aloe vera is in an amount of about 4% by weight, the citric acid is in an amount of less than 1.0% by weight, the water is in an amount of 30% by weight, the sodium benzoate is in an amount of 0.1% by weight and the fragrance is in an amount of 0.1% by weight.

Aloe vera is a juice from a South African lily-like plant used for its softening benefits in skin creams and its healing and soothing benefits on burned, irritated or damaged skin. In composition it is basically 99.5% water with the remaining 0.5% composed of 20 of 22 known amino acids, eight of which are considered essential to sustain growth and health; aloe vera has no known toxicity when applied to the skin. Alcohol is a compound found used in virtually all aftershave lotions, preshave lotions, deodorants and the like; it is used and performs as a solvent, antiseptic and drying agent since it is colorless and has a slight but pleasant odor compatible with any fragrance. The fragrance is preferably musk oil, or a derivative thereof, but can be an extract of a lime or generally any citrus extract used as a fragrance agent; said fragrances have no known toxicity when applied to the skin. Other fragrances with no known toxicity could also be used.

Propylene glycol is used for its colorlessness and property or characteristic of absorbing moisture, as well as acting as a solvent and being a wetting agent. Water is used as a base and thinning agent to prevent stickiness and unwanted strength in the composition.

Citric acid is a widely used agent in the cosmetic industry; it is a mild astringent, a foam inhibitor, adjusts the pH of the preparation, and most importantly, is used as a sequestering agent. In other words because the aloe vera is a plant product, the citrus component or citric acid is as a preservative to prevent physical or chemical changes affecting color, texture or appearance of the product. Sodium benzoate is a preservative commonly used and associated with aloe vera and is antiseptic in nature.

The ladies aftershave lotion of the invention with the ingredients combined as set forth provides a soothing and cooling effect on the skin after shaving, and the aloe vera therein particularly provides something that women desire that is not available as readily in related products. If the skin is rough and dry after shaving, it not only provides immediate relief and healing for tender skin areas, but leaves the skin soft and smooth to the touch.

The foregoing description is considered as illustrative only of the principles of the invention. Further, since numerous modifications and changes will readily occur to those skilled in the art, it is not desired to limit the invention to the exact preparation and method shown and described, and accordingly, all suitable modifications and equivalents may be resorted to fall within the scope of the invention.

What is claimed and desired to be secured by Letters Patent is:

1. An astringent, antiseptic, aloe containing ladies aftershave for application to tender areas such as legs and underarms, and the like, following the shaving of same, consisting essentially of:
    aloe vera in an amount of about 4% by weight;
    alcohol in an amount of about 55% by weight;
    propylene glycol in an amount of about 10% by weight;
    citric acid in an amount of less than 1% by weight;
    sodium benzoate in an amount of about 0.1% by weight; and
    water in an amount of about 30% by weight;
    a fragrance in an amount of about 0.1% by weight.

2. Method of making an astringent, antiseptic, aloe containing ladies' aftershave of claim 1 for application to tender areas such as legs and underarms and the like, following the shaving of same, consisting essentially of the steps of:
    mixing citric acid in an amount of less than 1.0% by weight and sodium benzoate in an amount of about 0.1% by weight with aloe vera in an amount of about 4% by weight;
    adding water in an amount of about 30% by weight to the above;
    adding alcohol in an amount of about 55% and propylene glycol in an amount of about 10%, by weight;
    mixing these thoroughly throughout, and
    adding fragrance in an amount of about 0.1% by weight.

* * * * *